United States Patent [19]
Hirose et al.

[11] Patent Number: 5,783,830
[45] Date of Patent: Jul. 21, 1998

[54] SAMPLE EVALUATION/PROCESS OBSERVATION SYSTEM AND METHOD

[75] Inventors: Hiroshi Hirose; Hidemi Koike; Shigeto Isakozawa; Yuji Sato; Mikio Ichihashi; Motohide Ukiana, all of Hitachinaka, Japan

[73] Assignee: Hitachi, Ltd., Tokyo, Japan

[21] Appl. No.: 873,788

[22] Filed: Jun. 12, 1997

[30] Foreign Application Priority Data

Jun. 13, 1996 [JP] Japan .................................. 8-152101
Jun. 13, 1996 [JP] Japan .................................. 8-152102

[51] Int. Cl.$^6$ ..................................................... H01J 37/20
[52] U.S. Cl. ........................... 250/492.21; 250/442.11
[58] Field of Search ........................... 250/492.21, 492.2, 250/398, 442.11, 440.11, 310, 311

[56] References Cited

U.S. PATENT DOCUMENTS

| | | | |
|---|---|---|---|
| 3,778,621 | 12/1973 | Mikajiri | 250/442 |
| 5,089,708 | 2/1992 | Asselbergs | 250/442.11 |

FOREIGN PATENT DOCUMENTS

| | | |
|---|---|---|
| 3263746A | 11/1991 | Japan . |
| 3272554A | 12/1991 | Japan . |
| 476437A | 3/1992 | Japan . |
| 4248237A | 9/1992 | Japan . |
| 4328233A | 11/1992 | Japan . |
| 6103947A | 4/1994 | Japan . |

*Primary Examiner*—Kiet T. Nguyen
*Attorney, Agent, or Firm*—Kenyon & Kenyon

[57] ABSTRACT

A sample evaluation/process observation system includes a common sample stage which accommodates a plurality of samples to be processed. The common sample stage is provided with a processing/observing notch and also with a movement mechanism. The movement mechanism functions to sequentially move the plurality of samples to the notch to cause the samples to be exposed to a predetermined processing beam and observing beam. The system further includes a beam processing device in which the common sample stage can be mounted and which functions to irradiate the predetermined processing beam on the plurality of samples through the notch to thereby sequentially perform beam processing operation over the samples. The system further includes a beam observation device in which the common sample stage can be mounted and which functions to irradiate the predetermined observing beam on the plurality of samples through the notch to sequentially observe and evaluate shapes of the plurality of samples. A mark is formed on one sample by a focused ion beam device so that positioning of the mark realizes automatic processing of a part of the sample to be processed. Further, the common sample stage is used in a high-acceleration transmission electron microscope and a high-acceleration scanning electron microscope and focused ion beam device.

9 Claims, 6 Drawing Sheets

SAMPLE EVALUATION/PROCESS OBSERVATION SYSTEM AND METHOD

BACKGROUND OF THE INVENTION

The present invention relates to a system for processing a sample by an ion beam and then observing the processed sample with use of an electron microscope or the like.

An example of prior art systems for processing a sample with use of a focused ion beam system and subsequently observing the processed sample is such a "focused ion beam system" as disclosed in JP-A-6-103947. According to a technique used in this ion beam system, the sample processed by the focused ion beam system can be inserted into a preprocessing device and an observation device without replacing it. When it is desired to prepare a sample in use for, e.g., a transmission electron microscope (TEM) in this system, however, the sample is required to be made as thin as about 100 nm, which sometimes results in that a location on the sample to be truly observed is undesirably cut off. In the case of semiconductor defect analysis, a defect is usually a single point on a fine portion and cutting off of such a defect point often leads to a lethal problem in its analysis.

Further, the aforementioned system is effective for a single sample but cannot cope with a plurality of samples. Therefore, the prior art system cannot process and observe a plurality of samples automatically. Meanwhile, prior art systems for observing a plurality of samples on a side entry stage of a transmission electron microscope (TEM) include such a "system for switching samples in used for an electron microscope" as disclosed in JP-A-4-248237 and such an "electron microscope" as disclosed in JP-A-4-328233. However, holders used in these prior arts are designed exclusively for the transmission electron microscope and no consideration is paid on sample processing. These prior arts fail to disclose sample automatic observation, though they disclose remote control based on motor drive.

Disclosed in JP-A-4-76437 is a focused charged-beam processing method for observing an SEM image of a sample if required in the course of processing the sample for its optimum processing in a composite system of the focused ion beam (FIB) system and the scanning electron microscope (SEM). In this method, the sample is partly cut off to observe the cut face and judge a processing position. For this reason, there is a danger that a desired location of the sample may be unfavorably cut off prior to the judgement. Further, this method requires the replacement of the sample between the processing and final observation, which disadvantageously results in that its replacing time is required and the sample replacement involves such trouble causes as damage or falling. Furthermore, the method provides a bad resolution for the SEM image because an energy at the time of observing the SEM image is low (about 10 kV).

SUMMARY OF THE INVENTION

It is therefore an object of the present invention to increase a material analysis speed by positively leaving an observation part of a sample without cutting off it and also to increase a processing efficiency by processing the sample between its processing and observing steps on an identical sample holder without replacing the sample on another holder.

Another object of the present invention is to process and observe a plurality of samples without replacing them to another holder. An related object of the present invention thereof is to automatically process or observe a plurality of samples.

In accordance with an aspect of the present invention, a sample is observed through a scanning transmission electron microscope (STEM) or a scanning electron microscope (SEM) attached to the transmission electron microscope (TEM) to acquire preliminary observation information including depth direction information and to determine a next processing point, processing dimensions, etc. based on the acquired information. In order to make the processing and observation more efficient, a common sample holder of a side entry type is employed so that only insertion and pulling out of the sample holder allow execution of the processing without sample replacement.

In accordance with another aspect of the present invention, for the purpose of observing a plurality of samples with use of, e.g., a transmission electron microscope (TEM), the samples are arranged so as not to be overlapped in their processing and observing surfaces. For the purpose of commonly using a sample holder, further, the sample holder is provided with a side entry type stage and both of processing and observing beams are arranged to reach an observation part. Automatic processing is carried out on the basis of a mark processed on a surface of a sample as a reference, whereas, automatic observation is carried out on the basis of a processing outer periphery or the like of the sample as a reference.

DESCRIPTION OF THE PREFERRED EMBODIMENTS

Figure 1:
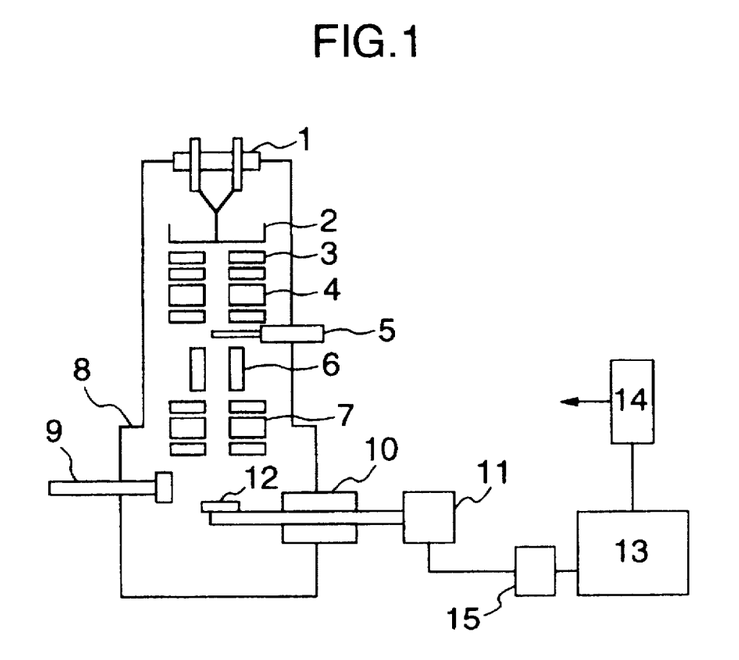
FIG. 1 schematically shows a sample processing apparatus for use in an embodiment of the present invention.

An embodiment of the present invention will be explained. Referring to FIG. 1, there is shown a focused ion beam system as a processing system in accordance with an embodiment of the present invention. A Ga ion beam emitted from an ion emitter 1 disposed in the center of a shield electrode 2 is accelerated to 30 KeV between the ion emitter 1 and a lead electrode 3, subjected by a diaphragm 5 to a beam angle restriction, and then focused on a sample (semiconductor device) 12 by a condenser lens 4 and an objective lens 7 as electrostatic lenses. The beam is controlled by a scanning electrode 6 with respect to its deflection to be used for image display and processing.

In the case of the image display, signal detection is carried out by a secondary particle detector 9. In the illustrated example, a plurality of the samples 12 are arranged on a sample holder 11. The sample holder 11 is passed through a sample fine moving device 10 and then inserted into a sample chamber 8. Devices including the sample holder 11 are driven under control of commands issued from a controller 13 through a control power source 14 and a sample driving power source 15.

Figure 2:
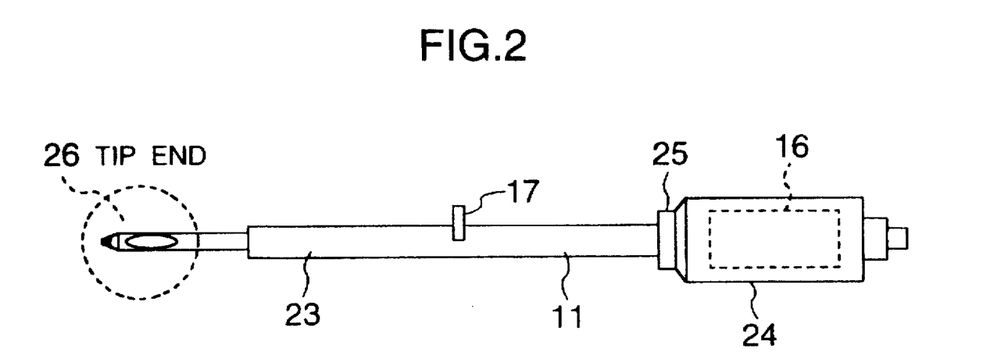
FIG. 2 is an external appearance of a sample holder used in the sample processing apparatus of FIG. 1.

Shown in FIG. 2 is details of the sample holder 11, i.e., so-called side entry stage holder. The sample holder 11 is provided with a knob 24, a rod 23, a pin 17 and a tip end 26. The knob 24 is provided therein with a sample rotary drive mechanism 16, and is provided at its one end with a graduation scale 25 indicative of a position of the sample 12.

Figure 3A:
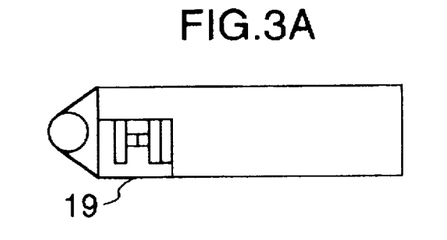
FIGS. 3A, 3B and 3C are plan, side and partially enlarged views of a part of a tip end of the sample holder.
Figure 3B:
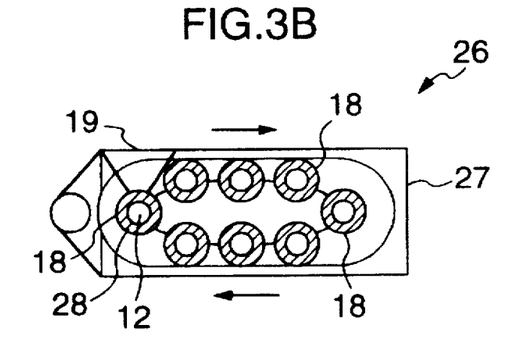
Figure 3C:
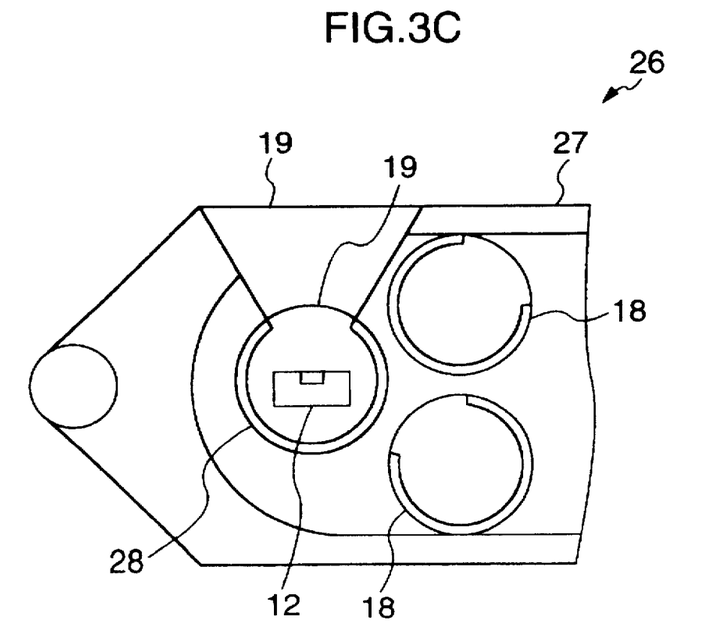

FIG. 3C shows an enlarged view of the tip end 26, wherein FIG. 3A is a plan view of the tip end of the sample holder 11 as viewed from an incident side of the processing beam, and FIG. 3B is a side view of FIG. 3A. The processing beam is guided through a processing beam opening 19 having a notch shape into the tip end 26 in a direction normal to a plane of a paper sheet of FIG. 3A and perpendicular to the longitudinal direction of the tip end 26. Meanwhile, an observing beam is irradiated on the sample 12 located at a processing observation point from a direction normal to a paper sheet of FIG. 3B (and FIG. 3C). The sample 12 corresponds to one of a plurality of (8 in the present embodiment) samples each arranged in an associated sample cell. The processing beam opening 19 is formed in each cell 18 and a cell holder 27 to be open as shown in FIG. 3C. The sample cells are arranged to be sequentially rotated in a direction shown by arrows in FIG. 3B, so that, when the sample 12 is positioned at a processing observation point 28, the cell holder 27 conforms to the processing beam opening 19 of the sample cell 18.

Figure 4:
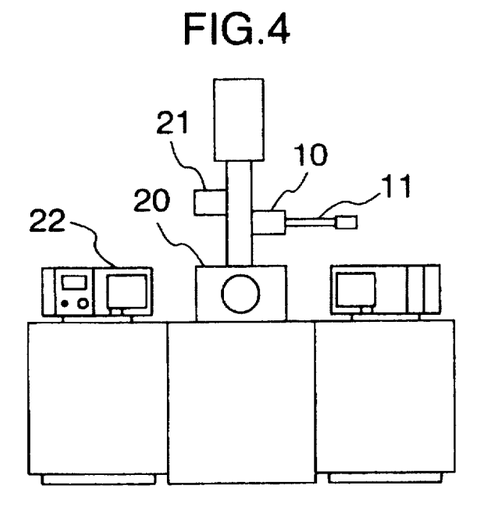
FIG. 4 schematically shows a transmission electron microscope.

Rotation of the sample cell is carried out by the sample rotary drive mechanism 16. As shown in FIG. 3C, sample 12 is disposed on cut-out mesh 32. The cut-out mesh is fixed within sample cell 18. The sample 12 is processed at a position corresponding to the processing observation point 28. The processing operation is carried out from a direction perpendicular to the paper sheet of FIG. 3A. When carrying out processing and observation of the sample by using the sample holder, it requires such a transmission electron microscope which allows use of the sample holder 11 used in the focused ion beam processing/observing system as it is. FIG. 4 shows the transmission electron microscope which is provided, in addition to a main body 20 of the transmission electron microscope, a SEM part 21 for image observation by a scanning electron microscope and a SEM image display unit 22 for image display by the scanning electron microscope. The sample holder 11 carrying thereon the sample processed with use of a focused ion beam is inserted through the sample fine moving device 10.

Figure 5A:
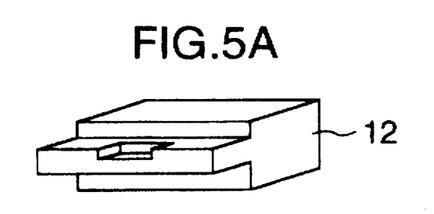
FIGS. 5A and 5B schematically show states of a sample after and before its processing.
Figure 6A:
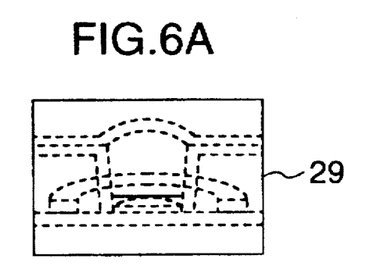
FIGS. 6A, 6B, 6C and 6D show observed states of the sample of FIGS. 5A and 5B after and before the processing.

The processing and observing procedures are as follows. The sample is first processed with use of the focused ion beam. A shape of the sample after processed is shown in FIG. 5A. The sample holder 11 is pulled out from the focused ion beam apparatus of FIG. 1 with the sample having the above shape (FIG. 5A) carried on the sample holder, and then inserted into the main body 20 of the transmission electron microscope of FIG. 4. The transmission electron microscope has an electron source of an electromagnetic emission type is utilized, having an electron acceleration voltage of 200 kV. Shown in FIG. 6A is an example of the sample 12 when observed from the same direction as the observation thereof with use of the transmission electron microscope 20 based on the SEM functions 21 and 22 attached to the transmission electron microscope 20. It will be seen that, since the SEM image uses a primary electron beam having the acceleration voltage of 200 kV, even if the processing depth does not reach the observation point, it slightly comes up thereto as shown by dotted lines in FIG. 6A since electron beam penetrate deeply. (In the display examples of FIGS. 6A to 6D, solid lines indicate information on the surface and dotted lines indicate information on the interior). Under this condition, since the observation point cannot be clearly observed, the sample holder is again returned to the focused ion beam apparatus for its additional processing. Through repetition of such additional FIB processing and TEM observation several times, the processing of one side of the sample 12 is completed.

Figure 5B:
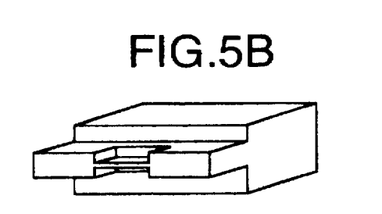
Figure 6B:
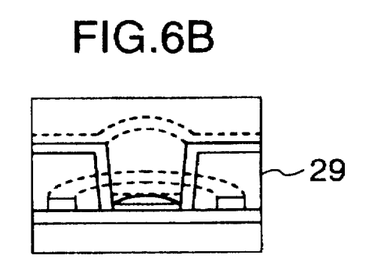

A result of the high-acceleration SEM image when observed under the above condition is shown in FIG. 6B. In FIG. 6B, the observation point clearly appears. Since the acceleration voltage is high, an electron probe can be made small in diameter and thus its resolution is good. In addition, since information on parts deeper than the surface can be obtained, it is possible to observe the sample 12 with its tilted condition and to measure a depth dimension from the observed value. Based on the measured dimension, the next processing dimension can be determined. At this stage, such a processing point as shown in FIG. 6B is judged to be good, and then a surface of the sample opposite to the surface in question is processed by the focused ion beam apparatus. In order to prevent the observation point from being cut off, the sample is initially processed to have a wall thickness of 100 to 200 nm (refer to FIG. 5B).

Figure 6C:
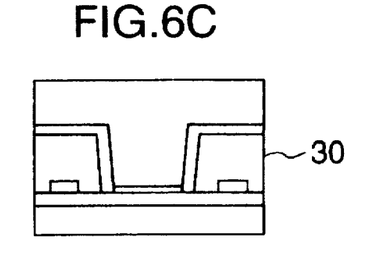
Figure 6D:
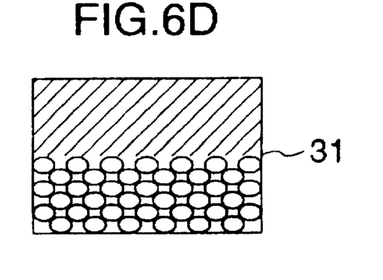

Now that the sample is made thin, observation of its TEM image is carried out, which result is shown in FIG. 6C. It is judged at this stage from FIG. 6C whether or not the sample is required to be further processed for thinner processing. In the illustrated example, the sample was further processed to have a wall thickness of 80 nm or less and eventually its atomic image was observed by increasing the observation magnification factor (refer to FIG. 6D).

In this way, in the case of the TEM observation, the thinner the sample is the better acquired data is, but when the sample is made thin, desired information may be sometimes lost. In such a case, with respect to even a thin sample, it is effective to use an energy filter TEM having a good contrast. A transmission electron beam of the transmission electron microscope, in the course of transmitting the material, inelastically collides with atoms in the sample, with a slight energy loss. Since the collision quantity varies depending on the sample structure or atom type, however, when the transmission electron beam is passed through an energy filter, it become possible to collect only electron beams with a regular energy loss, so that, even when the sample is thick, a featured contrast can be obtained.

Although the high-acceleration scanning electron microscope (SEM) and transmission electron microscope (TEM) have been used as preliminary observation means in the course of processing the sample in the present embodiment, it is also possible to use a scanning transmission electron microscope (STEM) when the sample becomes as thin as about several 100 nm. Similarly, even as its final observing means, the scanning electron microscope (SEM) and/or scanning transmission electron microscope (STEM) may be also used.

In the present embodiment, since the common rotary plural-sample holder is used, up to 8 samples can be processed and inserted into the transmission electron microscope at a time. When it is desired to process more than 8 samples, it is efficient to prepare a plurality of sample holders to use them for processing and observation separately. For the purpose of further increasing the efficiency, it is also possible to employ an automatic processing system.

Figure 7:
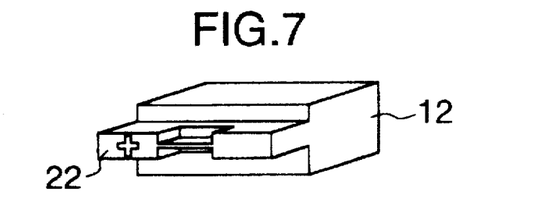
FIG. 7 shows a perspective view of the sample after eventually processed.

Explanation will be made as to how to process samples. It is assumed that a sample after processed has such a configuration as shown, e.g., in FIG. 7, in which case a mark 22' is applied to specify a processing position. The processing is carried out from a direction perpendicular to a plane of the mark, while observation thereof by the transmission electron microscope is carried out from a direction perpendicular to the processing direction. After one location is processed, the sample cell is rotated to shift the next sample to its processing/observing position, at which position the processing is again executed. In the embodiment shown in FIGS. 3A, 3B and 3C, samples up to 8 can be processed without breaking a vacuum condition thereof.

The samples after processed are pulled out of the focused ion beam apparatus on every sample holder basis and then the sample holder is inserted into the transmission electron microscope (see FIG. 4) for its observation. In this case, since the sample fine moving device 10 of the same type as the focused ion beam apparatus is used, the sample fine moving device 10 is the same even in the reproducibility of the sample position and thus the observation efficiency can be remarkably improved. Further, since up to 8 samples can be processed and observed, in this-example, without breaking the vacuum condition thereof, the efficiency can be expected to be increased to 8 times. When it is desired to further process the sample after observed, this can be realized only by inserting the holder 11 into the focused ion beam apparatus. In this case, since fine information on it by the transmission electron microscope is already grasped, the processing point becomes more clear, approaching to truly desired information.

Figure 8:
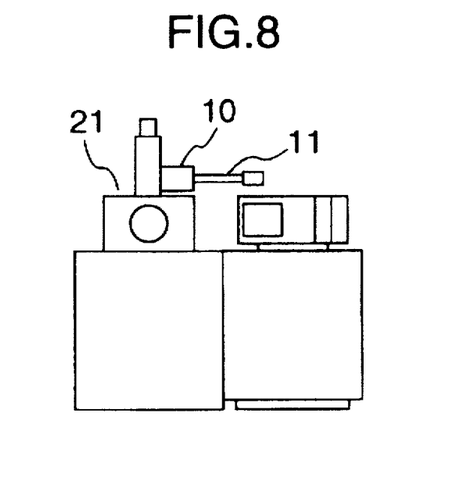
FIG. 8 schematically shows a scanning electron microscope.

Explanation will then be made in connection with an example in which a sample after processed is observed with use of a single scanning electron microscope. FIG. 8 shows an external appearance of a scanning electron microscope (SEM) 21. Like the transmission electron microscope, the sample fine moving device 10 of the same type as the scanning electron microscope is employed so that the sample holder 11 can be inserted into the scanning electron microscope as it is. With use of these device and microscope, information on a secondary electron image and transmitted electron image can be obtained. In the case of only the secondary electron image, it is unnecessary to make the sample thin, the processing become easier than the case of the TEM sample. Even in this case, the processing and observation can be realized over a plurality of samples without breaking a vacuum condition thereof, offering a great advantage.

Figure 9:
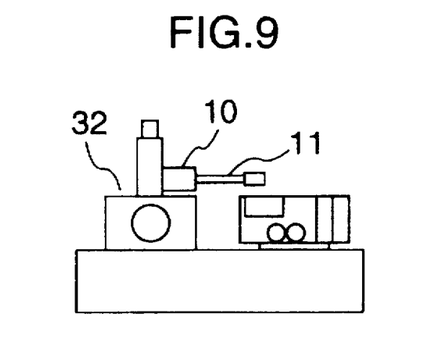
FIG. 9 schematically shows an ion milling device.

A sample surface processed by the focused ion beam apparatus tends to be microscopically destroyed in its crystalline structure or to have material chips generated during the processing attached thereonto, which is disadvantageous in its observation. In such a case, such a process as to irradiate a low-acceleration argon beam on the processed surface is required. In this connection, when the ion milling device is provided in the focused ion beam system, the sample is inserted into the ion milling device, and if not, the sample is inserted into ion milling device 32 (see FIG. 9) having the common sample holder 11. In the device of FIG. 9, processing of a plurality of samples can be carried out without breaking a vacuum condition thereof and also without replacing the samples.

Explanation will next be made as to automatic processing. If sample processing and observation, in particular, the time-consuming processing is automated, then the sample preparation efficiency will be remarkably improved. This respect is considered to the system of the present invention. An accuracy of rotating the sample cell 18 and moving it to the processing observation point 28 is at most several ten μm, whereas a requested processing position accuracy is below μm. For this reason, the present system was arranged so that the SEM image display unit 22 was applied as processed by the focused ion beam system to each of the samples in the sample cell and the processing position was determined based on the mark as a reference. The above mentioned procedure is controlled by controller 13 of FIB shown in FIG. 1.

Figure 10:
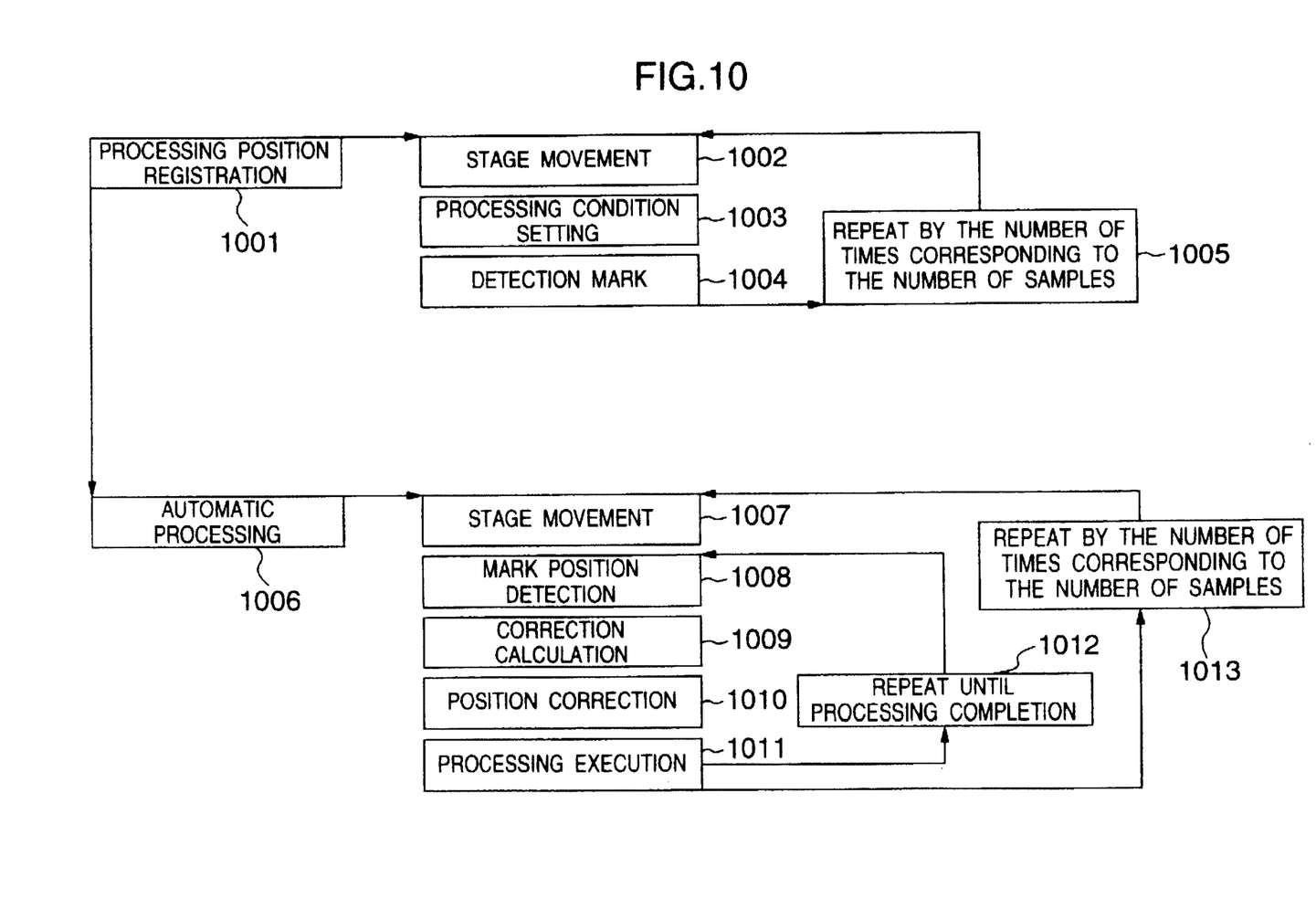
FIG. 10 is a flowchart for explaining automatic processing operation in the embodiment.

An embodiment of an automatic processing system is shown by a flowchart in FIG. 10. The automatic processing system is classified roughly into a processing position registration group (steps 1001 to 1005) and an automatic processing execution group (steps 1006 to 1012). In the processing position registration group; stage movement (step 1002), processing condition setting (step 1003) and detection mark preparation (step 1004) are carried out with respect to each sample, which steps are repeated BY the number of times corresponding to the number of samples (step 1005). In the automatic processing execution group; each sample placed on the sample holder is first subjected to a stage movement (step 1007) to move the sample to an FIB irradiation position, a position of the mark on the sample is detected (step 1008), a processing position of the sample is corrected (step 1009), and then the sample is subjected to a processing execution (step 1011). And a deviation in the processing position is eliminated by periodically interrupt the processing during the processing execution, detecting the mark position and correcting the position (steps 1008 to 1010).

The processing position registration and automatic processing execution are each repeated by the number of times corresponding to the number of samples mounted. This automatic processing is repeated for a plurality of samples, thus realizing the automatic processing. In this connection, it is not always necessary to periodically perform the mark position detecting operation for correction of the processing position, and the mark position detecting operation may be executed when the system catches a change in its operational condition.

Figure 11:
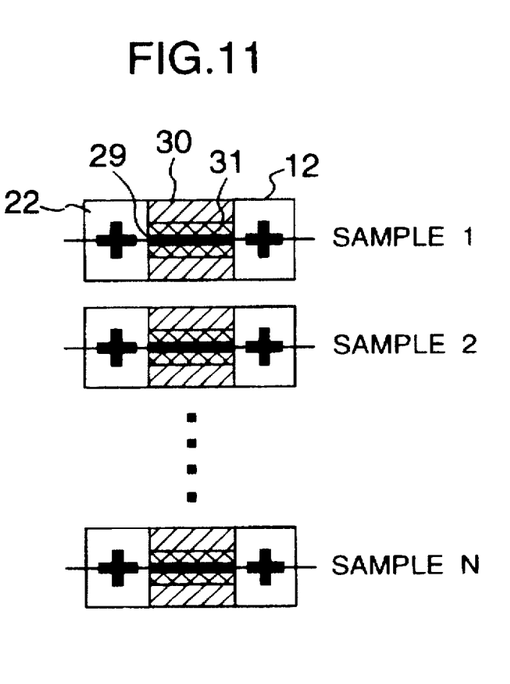
FIG. 11 schematically shows states of samples after roughly processed and during its processing.

FIG. 11 shows an embodiment when the present invention is applied to preparation of TEM samples.

Processing of a TEM sample by the focused ion beam device is generally divided into rough, intermediate and finish processings. In the embodiment of FIG. 11, rough processing 30 and intermediate processing 31 were respectively carried out from both sides (vertical direction) of an observation line 29 connecting centers of the marks 22 and 22. In this case, the automatic processing was possible, leaving a wall having a width of 0.2 m relative to the observation line 29 as its center line. Such processing, in many cases, requires about one hour per sample, though it also depends on its processing area. In such a case, when a feedback is generated based on observation information obtained by the transmission electron microscope or scanning electron microscope or when processing data is generated based on the observation information, the automatic processing can be realized even in such no worker absence as night time, thus remarkably improving its processing efficiency. Further, in the presence of the aforementioned mark on the sample during the automatic processing, even when the processing position is deviated by a stage lift or the like, the processing position can be corrected by periodically confirming the mark position.

Since observation by the transmission electron microscope or scanning electron microscope can be carried out relatively in a short time, the advantage resulting from the automation and night-time processing capability is not as great as the case of the FIB processing, but the automation capability is more convenient. In this case, the marks used in the automatic processing of the focused ion beam system are relatively moved to side faces from the observation face of the transmission electron microscope and scanning electron microscope as shown in FIG. 11. Accordingly, in order to use the mark 22 as an observation reference point, it is necessary to know a relation between the mark and observation point by providing a mark detecting function in a direction perpendicular to the observation beam or by processing a similar mark even on the perpendicular-direction plane (observation face of the transmission electron microscope and scanning electron microscope). When the observation point is relatively large and the entire processing area is to be observed, it is convenient to use its outer processing periphery as a reference. Thus, it is possible to determine the position in this manner, automatically determine observation conditions including focusing of the serving beam, and acquire specified information such as image information with respect to a plurality of samples. Sample exchange is carried out in a manner similar to in the processing mode.

In the foregoing embodiment, the sample cells 18 for holding samples were arranged to be rotatably moved but the sample cells are not always limited to the rotary arrangement. In an example of FIG. 12, the sample cells 18 are arranged linearly.

Figure 12:
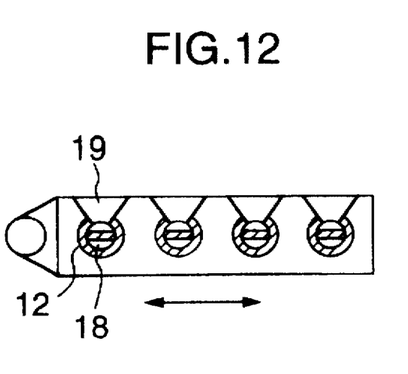
FIG. 12 schematically shows a linear sample holder.

In the latter case, the number of processing beam openings 19 is required to correspond to the number of samples. Since the linear arrangement simplifies the structure of the sample holder 11, a high rigidity can be secured for the sample holder, which is convenient when it is desired to observe the sample with a high resolution with use of the transmission electron microscope.

Further, even the linear arrangement of the cell holder may be modified in various ways, as when the cell holder is stationary and only the sample cells are linearly guided.

Furthermore, since the sample holder of the linear arrangement can hold thereon a plurality of samples, another sample can be processed during the irradiation of the processing or observing beam onto one sample. For example, while one sample is being processed, another sample may be subjected to the ion milling operation.

As has been explained in the foregoing, in accordance with the foregoing embodiment, when it is desired to determine a final processing position, this is determined by judging from preliminary observation information including information on the depth direction of the processing position of the sample, thereby avoiding such a danger as to cut off the processing target position.

Further, since samples can be transported on every sample holder during a period between the processing and observation works, not only a processing efficient can be improved but also such problems of sample falling, damage, missing or pollution can be minimized.

Furthermore, when a side entry type rotary holder is employed, automatic processing can also be realized for a plurality of samples and its analysis efficiency can be improved.

In addition, since processing automation and observation automation after the processing can be realized, such no-worker processing as in night time can be possible.

What is claimed is:

1. A sample valuation/process observation system comprising:

a common sample stage for accommodating a plurality of samples to be processed, said common sample stage having a processing/observing notch formed therein and also having a movement mechanism for sequentially moving said plurality of samples to said processing/ observing notch to cause the samples to be sequentially exposed to a predetermined processing beam and observing beam;

a beam processing device capable of having said common sample stage removably mounted thereto for irradiating a predetermined processing beam on said plurality of samples through said processing/observing notch to perform arbitrary sequential beam processing over said plurality of samples; and a beam observation device capable of having said common sample stage removably mounted thereto for irradiating said predetermined observing beam on said plurality of samples through said processing/observing notch to sequentially evaluate and observe shapes of said plurality of samples.

2. A sample evaluation/process observation system as set forth in claim 1, wherein said beam processing device is a focused ion beam device, and said beam observation device is any one of a scanning electron microscope, a transmission electron microscope and a scanning transmission electron microscope.

3. A sample evaluation/process observation system as set forth in claim 2, wherein an observation image by said scanning electron microscope is obtained from an electron beam of said transmission electron microscope.

4. A sample evaluation/process observation system as set forth in claim 1, wherein the sample to be processed is positioned at said processing/observing notch so that a surface of the sample to be subjected to irradiation of said processing beam to be processed makes an angle of about 90 degrees with respect to an observation surface of the sample to be subjected to irradiation of said observing beam.

5. A method for processing a plurality of samples with use of a focused ion beam device, said focused ion beam device comprising:

a common sample stage for accommodating said plurality of samples to be processed, said common sample stage having a processing/observing notch formed therein and also having a movement mechanism for sequentially moving said plurality of samples to said processing/ observing notch to cause the samples to be sequentially exposed by a predetermined processing beam and observing beam; and a beam processing device capable of having said common sample stage removably mounted thereto for irradiating a predetermined processing beam on said plurality of samples through said processing/observing notch to perform arbitrary sequential beam processing over said plurality of samples, said method including the steps of:

moving said plurality of samples to said processing/ observing notch on every plural-sample-on-stage basis and positioning them at their processing and observing positions;

forming a positioning detection mark at a predetermined position on each sample;

sequentially moving the samples already formed with said positioning detection mark to said processing/ observing notch and positioning each sample on the basis of said positioning detection mark; and ion-beam processing the samples with use of an ion beam on the basis of processing conditions set for each of the samples.

6. A method for processing a plurality of samples with use of a focused ion beam device as set forth in claim 5, wherein said ion-beam processing step includes a step of detecting said positioning detection mark at predetermined timing, a step of calculating a position correction on the basis of said positioning detection mark, and a step of performing the position correction over the sample to be processed on the basis of said calculated position correction.

7. A method for processing a plurality of samples with use of a focused ion beam device as set forth in claim 6, wherein said positioning detection mark is processed and formed through the ion beam processing on a surface of the sample intersecting a processing surface of the sample at an angle of about 90 degrees, said positioning detection mark is detected by a secondary particle detector to perform the positioning of the sample.

8. A sample evaluation method including the steps of:

accommodating a plurality of samples to be processed in a common sample stage having a processing/observing notch formed therein and also having a movement mechanism, said movement mechanism functioning to sequentially move said plurality of samples to said processing/observing notch to cause the samples to be exposed to a predetermined processing beam and observing beam;

mounting said common sample stage in a focused ion beam device, moving said plurality of samples to said processing/observing notch and irradiating a predetermined focused ion beam thereon for arbitrary beam processing;

mounting said common sample stage in a high-acceleration transmission electron microscope or a high-acceleration scanning electron microscope and confirming information on a thickness of the sample; and performing said ion processing step with use of said focused ion beam device and said step of confirming the thickness information with use of said high-acceleration focused ion beam or said high-acceleration transmission electron microscope, after passage of at least one processing cycle for final observation of the processed part.

9. A sample evaluation method as set forth in claim 8, wherein said final observation is carried out with use of any one of a transmission electron microscope, a scanning electron microscope and a scanning transmission electron microscope.

* * * * *